US006998501B1

(12) United States Patent
Wright et al.

(10) Patent No.: US 6,998,501 B1
(45) Date of Patent: Feb. 14, 2006

(54) NUTRITIONAL SUPPLEMENT FOR LOWERING SERUM TRIGLYCERIDE AND CHOLESTEROL LEVELS

(75) Inventors: Jeffrey L. C. Wright, Wilmington, NC (US); Jaroslav A. Kralovec, Halifax (CA)

(73) Assignee: Ocean Nutrition Canada Limited, Halifax (CA)

( * ) Notice: Subject to any disclaimer, the term of this patent is extended or adjusted under 35 U.S.C. 154(b) by 369 days.

(21) Appl. No.: 10/070,181

(22) PCT Filed: Aug. 30, 2000

(86) PCT No.: PCT/CA00/01011

§ 371 (c)(1),
(2), (4) Date: Jul. 8, 2002

(87) PCT Pub. No.: WO01/15552

PCT Pub. Date: Mar. 8, 2001

Related U.S. Application Data

(63) Continuation-in-part of application No. 09/385,834, filed on Aug. 30, 1999.

(51) Int. Cl.
*C07C 69/74* (2006.01)
(52) U.S. Cl. .............................................. 560/5; 560/7
(58) Field of Classification Search ................ 426/611; 514/182; 560/205, 217, 225
See application file for complete search history.

(56) References Cited

U.S. PATENT DOCUMENTS

| | | | |
|---|---|---|---|
| 4,526,902 A * | 7/1985 | Rubin | 514/560 |
| 4,588,717 A | 5/1986 | Mitchell | |
| 4,681,896 A * | 7/1987 | Horrobin | 514/552 |
| 4,879,312 A * | 11/1989 | Kamarei et al. | 514/460 |
| 5,059,622 A * | 10/1991 | Sears | |
| 5,502,045 A * | 3/1996 | Miettinen et al. | 514/182 |
| 5,593,691 A | 1/1997 | Eugster et al. | |
| 5,604,216 A * | 2/1997 | Horrobin | 514/182 |
| 5,770,749 A * | 6/1998 | Kutney et al. | 552/545 |
| 5,892,068 A | 4/1999 | Higgins, III | 552/554 |
| 5,965,449 A * | 10/1999 | Novak | 436/71 |
| 6,106,886 A * | 8/2000 | van Amerongen et al. | 426/611 |
| 6,147,236 A * | 11/2000 | Higgins, III | 552/554 |
| 6,162,483 A * | 12/2000 | Wester | 426/607 |
| 6,184,397 B1 * | 2/2001 | Roden et al. | 552/200 |
| 6,544,973 B1 | 4/2003 | Miettenen et al. | |
| 6,589,588 B1 * | 7/2003 | Wester et al. | 426/607 |
| 2002/0016314 A1 * | 2/2002 | Schersl | 514/169 |
| 2002/0055493 A1 * | 5/2002 | Burdick et al. | 514/169 |
| 2002/0160990 A1 * | 10/2002 | Burdick et al. | 514/182 |
| 2003/0054082 A1 * | 3/2003 | Koike et al. | 426/601 |
| 2003/0198727 A1 * | 10/2003 | Koike et al. | 426/601 |
| 2004/0052920 A1 * | 3/2004 | Koike et al. | 426/601 |
| 2004/0062847 A1 * | 4/2004 | Koike et al. | 426/601 |

FOREIGN PATENT DOCUMENTS

| | | |
|---|---|---|
| CA | 2102112 | 11/1992 |
| CA | 1337548 | 11/1995 |
| EP | 0 594 612 B1 | 5/1991 |
| EP | 0594612 B1 | 5/1991 |
| EP | 9 703 329 | 2/1997 |
| EP | 9703329 | 2/1997 |
| EP | 0 897 970 A1 | 2/1999 |
| EP | 0897970 | 2/1999 |
| EP | 897970 A1 * | 2/1999 |
| EP | 0982315 | 3/2000 |
| EP | 09826315 | 3/2000 |
| EP | 1004594 * | 5/2000 |
| WO | WO9735594 | 10/1987 |
| WO | 9219640 * | 11/1992 |
| WO | WO 92/19640 | 11/1992 |
| WO | WO9219640 | 11/1992 |
| WO | WO9806714 | 2/1996 |
| WO | WO 96/10033 | 4/1996 |
| WO | WO9510033 | 4/1996 |
| WO | WO9610033 | 4/1996 |
| WO | WO 96/38047 A1 | 12/1996 |
| WO | WO 9638047 A1 * | 12/1996 |
| WO | WO 97/35594 | 10/1997 |
| WO | WO9735594 | 10/1997 |
| WO | WO 98/01759 | 1/1998 |
| WO | WO9801759 | 1/1998 |
| WO | 9806405 | 2/1998 |
| WO | WO 98/06714 | 2/1998 |
| WO | WO9806714 | 2/1998 |
| WO | WO 98/18429 | 5/1998 |
| WO | WO9818429 | 5/1998 |
| WO | WO 99/30569 | 6/1999 |
| WO | WO9930569 | 6/1999 |
| WO | 0004887 | 2/2000 |

OTHER PUBLICATIONS

Lo et al., JAOCS, 60, 4, 1983.*
Higashidate et al. (Journal of Chromatography (1990), 515, 295-303).*

(Continued)

*Primary Examiner*—Johann Richter
*Assistant Examiner*—Karl Puttlitz
(74) *Attorney, Agent, or Firm*—Needle & Rosenberg, P.C.

(57) ABSTRACT

Triglycerides and cholesterol in the bloodstream are important factors in the development of cardiovascular disease. The present invention discloses a nutritional supplement comprising a sterol and an omega-3 fatty acid, or an ester thereof, for lowering cholesterol and triglyceride levels in the bloodstream of a subject. Preferably, the sterol and omega-3 fatty acid are together in the form of an ester.

12 Claims, No Drawings

OTHER PUBLICATIONS

Mishkel et al. (Bailliere's Clinical Haematology, vol. 3, No. 3, Jul. 1990, pp 625-649).*

Saynor et al., Changes in Blood Lipids and Fibrinogen with a Note on Safety in a Long Term Stdy on the Effects of n-3 Fatty Acids in Subjets Receiving Fish Oil Supplements and Followed for Seven Years, LIPIDS, vol. 27, No. 7, (1992), 533.*

International Search Report.

Rompp Chemie Lexicon. (1995) Georg Thieme Verlag, Germany, Table 2 on p. 272 (English translation provided).

Nguyen, Tu T.; "The Cholestrol-Lowering Action of Plant Stanol Esters," American Society for Nutritional Sciences, 1999.

Stalenhoef, Anton F.H., et al.; "The effect of concentrated n-3 fatty acids versus gemfibrozil on plasma lipoproteins, low density lipoprotein heterogeneity and ozidizability in patients with hypertrygliceridemia," Atherosclerosis, vol. 153, 2000, pp. 129-138.

Mattson, Fred H., et al., "Optimizing the effect of plant sterols on cholesterol absorption in man[1-3]", The American Journal of Clinical Nutrition (1982) 35:697-700.

Gould, R. Gordon, et al., "Absorbability of β-Sitosterol in Humans", Metabolism, (1969) vol. 18, No. 8, pp. 652-662.

Lo, Y. C., et al., "Physical and Chemical Properties of Randomly Interesterified Blends of Soybean Oil and Tallow for Use as Margarine Oils[1,2]", JAOCS, (1983) vol. 60, No. 4, pp. 815-818.

Sreenivasan, B., "Interesterification of Fats" JAOCS, (1978) vol. 55, pp. 796-805.

Chobanov, D., et al., "Alterations in Glyceride Composition During Interesterification of Mixtures of Sunflower Oil with Lard and Tallow", JAOCS, (1977), vol. 54, pp. 47-50.

Saynor, Reginald, et al., "Changes in Blood Lipids and Fibrinogen with a Note on Safety in a Long Term Study on the Effects of n-3 Fatty Acids in Subjects Receiving Fish Oil Supplements and Followed for Seven Years", (1992) Lipids, vol. 27, No. 7, pp. 533-538.

Gylling, Helena, et al., "Sitostanol ester margarine in dietary treatment of children with familial hypercholesterolemia" (1995) Journal of Lipid Research, vol. 36, pp. 1807-1812.

Gylling, H., et al., "Serum cholesterol and cholesterol and lipoprotein metabolism in hypercholesterolaemic NIDDM patients before and during sitostanol ester-margarine treatment", (1994) Diabetologia 37:773-780.

Vanhanen, H., "Cholesterol malabsorption caused by sitostanol ester feeding and neomycin in pravastatin-treated hypercholesterolaemic patients", (1994), Eur. J. Clin. Pharmacol., 47:169-176.

Denke, Margo A., "Lack of efficacy of low-dose sitostanol therapy as an adjunct to a cholesterol-lowering diet in men with moderate hypercholesterolemia[1-3]", (1995) Am. J. Clin. Nutr. 61:392-6.

Tilvis, Reijo S., "Serum plant sterols and their relation to cholesterol absorption[1,2]", (1986), The American Journal of Clinical Nutrition, 43:92-97.

Moghadasian, Mohammed H., et al., "Tall Oil"—Derived Phytosterols Reduce Atherosclerosis in ApoE-Deficient Mice, (1997), vol. 17(1), pp. 119-126.

"Dietary Supplementation with n-3 Polyunsaturated Fatty Acids and Vitamin E after Myocardial Infarction: Results of the GISSI-Preventione Trial," The Lancet, 354:447-455 (1999).

"Randomised Trial of Cholesterol Lowering in 4444 Patients with Coronary Heart Disease: The Scandinavian Simvastatin Survival Study (4S)," The Lancet vol. 344, Nov. 19, 1383-1389 (1994).

Burr, M.L. et al., "Effects of Changes in Fat, Fish, and Fibre Intakes on Death and Mycocardial Reinfarction: Diet and Reinfarction Trial (Dart)," The Lancet, 757-761 (1989).

Carey, Martin C. et al., "Lipid Digestion and Absorption," Ann. Rev. Physiol. 45:651-77 (1983).

Connor, Sonja L. et al., "Are Fish Oils Beneficial in the Prevention and Treatment of Coronary Artery Disease?"Am. J. Clin. Nutr. 66 (Suppl.): 1020S-31S (1997).

Criqui, M.H., "Triglycerides and Cardiovascular Disease, A Focus on Clinical Trials," European Heart Journal 19 (Supplement A); A36-A39.

Eisenberg, Daniel, "The Importance of Lowering Cholesterol in Patients with Cornary Heart Disease," Clin. Cardiol. 21:81-84 (1998).

Franceschini, G. et al, "Pharmacological Control of Hypertriglyceridemia," (1993) Cardiovas. Drugs Ther., 7, 297-302.

Gotto, Antonio M., Jr., "Triglyceride, The Forgotten Risk Factor," Circulation, 97: 1027-1028 (1998).

Grundy, Scott M., "Hypertiglyceridemina, Atherogenic Dyslipidemia, and the Metabolic Syndrome," American Journal of Cardiology, 81 (4A): 18B-25B (1998).

Grundy, Scott M., "Small LDL, Atherogenic Dyslipidemia, and the Metabolic Syndrome," Circulation 95:1-4 (1997).

Guido Franceschini and Rodolfo Paoletti, "Pharmacological Control of Hypertriglyceridemia," Cardiovascular Drugs and Therapy, 1993:7:297-302 (1993).

Harris, William S., "Fish Oils and Plasma Lipid and Lipoprotein Metabolism in Humans: A Critical Review," Journal of Lipid Research, 30:785-807 (1989).

Heinemann T. et al., "Effect of Low-Dose Sitostanol on Serum Cholesterol in Patients with Hypercholesterolemia," Arethrosclerosis 61:216-223 (1986).

Heinemann, T. et al., "Mechanisms of Action of Plant Sterols on Inhibition of Cholesterol Absorption, Comparison of Sitosterol and Sitostanol," European Clinical Pharmacology, vol. 40: Suppl. 1:S59-S63 (1991).

Jeppesen, Jorgen et al., "Triglyceride Concentration and Ischemic Heart Disease, An Eight-Year Follow-up in the Copenhagen Male Study," Circulation 97:1029-1036 (1998).

Jones, Peter et al., "Dietary Phytosterols as Cholesterol-Lowering Agents in Humans," Can. J. Physiol. Pharmacol. 75:217-227 (1997).

Kinsella, John E. et al., "Dietary n-3 Polyunsaturated Fatty Acids and Amelioration of Cardiovascular Disease: Posible Mechansims[1-3]," Am. J. Clinic. Nutr., 52:1-28 (1990).

Leaf, Alexander et al.,"Medical Progress, Cardiovascular Effects of n-3 Fatty Acids," The New England Journal of Medicine, No. 9, 318:549-557 (1988).

Ling, W.H. et al., "Dietary Phytosterols: A Review of Metabolism, Benefits and Side Effects," Life Sciences vol. 57, No. 3: 195-296 (1995).

Miettinen, Tatu et al, "Regulation of Cholesterol Metabolism by Dietary Plant Sterols," Current Opinion in Lipidology, 10:9-14 (1999).

Mishkel, Gregory J. et al., "Cardiovascular Effects of ω-3 Polyunsaturated Fatty Acids (Fish Oils)", Bailliere's Clinical Haematology, No. 3, 3:625-649 (1990).

Sacks, Frank M. et al., "The Effect of Pravastatin on Coronary Events After Myocardial Infarction in Patients with Average Cholesterol Levels," The New England Journal of Medicine, vol. 335: 1001-9 (1996).

Shimada et al., "Enzymatic Synthesis of Steryl Esters of Polyunsaturated Fatty Acids," *J. American Oil Chemists*, vol. 76, No. 6 Jun. 1999 pp. 713-716.

Shepherd, James et al., "Prevention of Coronary Heart Disease with Pravastatin in Metn with Hypercholesterolemia," *The New England Journal of Medicine*, vol. 333, 1301-1307 (1995).

Vanhanen, H.T. et al., "Serum Levels, Absorption Efficiency, Faecal Elimination and Synthesis of Cholesterol During Increasing Doses of Dietary Sitostanol Esters in Hypercholesterolaemic Subjects," *Clinical Science*, 87:61-67 (1994).

Vanhanen, Hannu T. et al., "Serum Cholesterol, Cholesterol Precursors, and Plant Sterols in Hypercholesterolemic Subjects with Different apoE Phenotypes During Dietary Sitostanol Ester Treatment," *Journal of Lipid Research*, 34:1535-1544 (1993).

von Shacky, Clemens et al., "The Effect of Dietary $\omega$-3 Fatty Acids on Coronary Atherosclerosis, A Randomized, Double-Blind, Placebo-Controlled Trial," *Annals of Internal Medicine*, 130:554-562 (1999).

Criqui M.H., "Triglycerides and Cardiovascular Disease, A Focus on Clinical Trials", *European Heart Journal* 19 (Supplement A); A36-A39.

Grundy, Scott M., "Hypertriglyceridemia, Atherogenic Dyslipidemia, and the Metabolic Syndrome", *American Journal of Cardiology*, 81(4A):18B-25B.

Gotto, Antonio M., Jr., "Triglyceride, The Forgotten Risk Factor", *Circulation*, 97:1027-1028 (1998).

Shepherd, James, et al., "Prevention of Coronary Heart Disease With Pravastatin in Men With Hypercholesterolemia", *The New England Journal of Medicine*, vol. 333:1301-7 (1995).

Sacks, Frank, M., et al., "The Effect of Pravastatin on Coronary Events After Myocardial Infarction in Patients with Average Cholesterol Levels", *The New England Journal of Medicine*, vol. 335:1001-9 (1996).

Heinemann, T., et al., "Mechanisms of Action of Plant Sterols on Inhibition of Cholesterol Absorption, Comparison of Sitosterol and Sitostanol", *European Clinical Pharmacology*, vol. 40: Suppl. 1:S59-S63 (1991).

Ling, W.H., et al., "Dietary Phytosterols: A Review of Metabolism, Benefits and Side Effects", *Life Sciences*, vol. 57, No. 3:195-296 (1995).

Jones, Peter, J.H., et al., "Dietary Phytosterols as Cholesterol-Lowering Agents in Humans", *Can. J. Physiol. Pharmacol.* 75:217-227 (1997).

Vanhanen, Hannu, T., et al., "Serum Cholesterol, Cholesterol Precursors, and Plant Sterols in Hypercholesterolemic Subjects with Different apoE Phenotypes During Dietary Sitostanol Ester Treatment", *Journal of Lipid Research*, 34:1535-1544 (1993).

Miettinen, Tatu, A., et al., "Regulation of Cholesterol Metabolism by Dietary Plant Sterols", *Current Opinion in Lipidology*, 10:9-14 (1999).

Vanhanen, H.T., et al., "Serum Levels, Absorption Efficiency, Faecal Elimination and Synthesis of Cholesterol During Increasing Doses of Dietary Sitostanol Esters in Hypercholesterolaemic Subjects", *Clinical Science*, 87:61-67 (1994).

Leaf, Alexander, et al., "Medical Progress, Cardiovascular Effects of n-3 Fatty Acids", *The New England Journal of Medicine*, No. 9, 318:549-557 (1988).

Mishkel, Gregory, J., et al., "Cardiovascular Effects of $\omega$-3 Polyunsaturated Fatty Acids (Fish Oils)", *Bailliere's Clinical Haematology*, No. 3, 3:625-649 (1990).

Kinsella, John, E., et al., Dietary n-3 Polyunsaturated Fatty Acids and Amelioration of Cardiovascular Disease: Possible Mechanisms[1-3], *Am. J. Clin. Nutr.*, 52:1-28 (1990).

Connor, Sonja, L., et al., "Are Fish Oils Beneficial in the Prevention and Treatment of Coronary Artery Disease?", *Am. J. Clin. Nutr.* 66 (Suppl.) :1020S-31S (1997).

Burr, M.L., et al., Effects of Changes in Fat, Fish, and Fibre Intakes on Death and Myocardial Reinfarction: Diet and Reinfarction Trial (Dart), *The Lancet*, 757-761 (1989).

von Shacky, Clemens, et al., "The Effect of Dietay $\omega$-3 Fatty Acids on Coronary Atherosclerosis, A Randomized, Double-Blind, Placebo-Controlled Trial", *Annals of Internal Medicine*, 130:554-562 (1999).

Harris, William, S., "Fish Oils and Plasma Lipid and Lipoprotein Metabolism in Humans: A Critical Review", *Journal of Lipid Research*, 30:785-807 (1989).

Carey, Martin, C., et al., "Lipid Digestion and Absorption" *Ann. Rev. Physiol.* 45:651-77 (1983).

Shimada, Yuji et al. "Enzymatic Synthesis of Steryl Esters of Polyunsaturated Fatty Acids". *JAOCS* 76(6):713-716 (1999).

Moghadasian, Mohammed H., et al., "Tall Oil,"—Derived Phytosterols Reduce Atherosclerosis in ApoE-Deficient Mice, (1997), vol. 17(1), pp. 119-126.

Heinemann, T., et al., "Effect of Low-Dose Sitostanol on Serum Cholesterol in Patients with Hypercholesterolemia", *Arethrosclerosis* 61:219-223 (1986).

International Search Report.

Rompp Chemie Lexicon. (1995) Georg Thieme Verlag, Germany, Table 2 on page 272 (English translation provided).

* cited by examiner

NUTRITIONAL SUPPLEMENT FOR LOWERING SERUM TRIGLYCERIDE AND CHOLESTEROL LEVELS

CROSS-REFERENCE TO RELATED APPLICATIONS

This application is filed under 35 U.S.C. § 371, and receives the benefit of International Application No. PCT/CA00/01011, filed Aug. 30, 2000 which is a continuation-in-part of application Ser. No. 09/385,834, filed Aug. 30, 1999.

FIELD OF THE INVENTION

The invention relates to control of cholesterol and triglyceride levels in mammals, particularly humans.

BACKGROUND OF THE INVENTION

Serum cholesterol and serum triglyceride levels are important factors in the development of cardiovascular disease. In many clinical studies there is a positive correlation between plasma triglycerides and the incidence of cardiovascular disease [1]. Elevated plasma triglyceride level is frequently associated with other atherogenic factors including elevated low-density lipoprotein (LDL)-cholesterol, reduced high-density lipoprotein (HDL)-cholesterol, and small LDL particles [2, 3]. There is growing acceptance that triglycerides act in a synergistic fashion with these other lipid risk factors to increase the incidence of cardiovascular disease [4, 5]. Hypertriglyceridemia usually occurs because of insulin resistance, which leads to overproduction of very low-density lipoproteins (VLDL) by the liver [3]. Treatment involves lifestyle changes to decrease body weight and to increase physical activity, both of which improve insulin sensitivity. Drug therapy to lower triglycerides involves the use of fibrates or nicotinic acid [6].

A number of clinical studies convincingly establish plasma cholesterol and LDL-cholesterol as independent risk factors for coronary heart disease [7]. Pharmacological agents, called statins, lower total plasma cholesterol by inhibiting the synthesis of cholesterol by the liver. The statins reduce the morbidity and mortality rate from cardiovascular disease in high risk, hypercholesterolemic patients [8, 9], but also in persons who exhibit "average" cholesterol levels [10]. Another approach is to interfere with the intestinal absorption of cholesterol. Certain phytosterols (plant sterols) such as stigmasterol and β-sitosterol lower serum cholesterol act by inhibiting absorption of both dietary and biliary cholesterol from the small intestine [11].

With respect to the most appropriate form of phytosterols for lowering serum cholesterol, some reports indicate that free phytosterols reduce serum cholesterol in animals and humans [12, 13]. However, there is also evidence to indicate that a sterol esterified with a fatty acid may be more effective [14]. Trials show that phytosterol esters of plant fatty acids obtained from canola oil, when incorporated into food such as margarine or mayonnaise, lower total cholesterol and LDL-cholesterol levels by about 10 and 15 percent, respectively [15, 16]. U.S. Pat. No. 5,502,045 (Miettinen et al., issued Mar. 26, 1996) discloses the use of sitostanol esters of canola oil to lower serum cholesterol. Benecol™(Raisio Benecol Ltd., Raisio, Finland), a margarine that contains such compounds, is now on the market.

The mechanism by which phytosterols or phytosterol esters inhibit absorption of dietary cholesterol by the digestive tract is not fully understood but may involve competitive inhibition of cholesterol uptake from the intestinal lumen or inhibition of cholesterol esterification in the intestinal mucosa [12]. It is known that phytosterols themselves are only poorly absorbed. Vanhanen et al. [17] report that phytosterol esters may also be poorly absorbed by the intestinal tract based on postprandial measurements of β-sitostanol in plasma. A direct measure of phytosterol ester uptake by the digestive tract has not been reported.

When phytosterols are esterified with fatty acids from plant sources such as canola, the long-chain polyunsaturated fatty acids (LCPUFAs) that are incorporated are predominantly of the omega-6 series. Omega-6 fatty acids do not affect plasma triglycerides. Research to date on fatty acid esters of sterols has focused only on the efficacy of the sterol in lowering cholesterol.

SUMMARY OF THE INVENTION

The present invention provides a nutritional supplement comprising a sterol and an omega-3 fatty acid, or an ester thereof, for lowering cholesterol and triglyceride levels in the bloodstream of a subject.

The present invention also provides a method of lowering cholesterol and triglyceride levels in the bloodstream of a subject, the method including the step of administration of an effective amount of a nutritional supplement comprising a sterol and an omega-3 fatty acid, or an ester thereof, to a subject.

The present invention also provides the use of the nutritional supplement defined herein for lowering cholesterol and triglyceride levels in the bloodstream of a subject.

The subject is preferably a mammal, more preferably a human.

The present invention further provides a foodstuff composition comprising the nutritional supplement defined herein and a foodstuff, the nutritional value of the foodstuff belong enhanced by incorporation of the nutritional supplement defined herein.

The present invention further provides the use of the nutritional supplement defined herein in the manufacture of a foodstuff composition.

The present invention further provides a process for preparing the nutritional supplement as defined herein, which comprises the step of reacting a sterol with an omega-3 fatty acid, or an ester thereof, in the presence of a base.

Base catalysts were found to be successful in the transesterification (or interesterification) process of the invention. Such a reaction is advantageous given the availability of esterified omega-3 fatty acid starting material, for example from fish oil. In addition, acidic catalysts were found to be ineffective in the transesterification of interest.

Sterols are not very soluble in lipid, which complicates their use in lipid-based foods. A mixture of a sterol and a free omega-3 fatty acid, which typically forms a paste at a molar ratio of 1:1, may be used. If a mixture is used, the omega-3 fatty acid can be a free acid or can be in ester form, preferably a succinimidyl, triglyceride, ($C_3$–$C_{12}$)cycloalkyl or ($C_1$–$C_8$)alkyl ester, more preferably an ethyl ester. In the mixture, the molar ratio range of omega-3 fatty acid, or an ester thereof, to sterol should be about 0.5 to 8, preferably 0.76 to 6.4, more preferably 1 to 2.

Preferably, the sterol and the omega-3 fatty acid are together in the form of an ester. The sterol esters of the present invention are highly fat-soluble and represent a bifunctional species, since they lower both serum cholesterol and serum triglyceride levels in the bloodstream.

DETAILED DESCRIPTION OF THE PREFERRED EMBODIMENTS

The sterols used to prepare the nutritional supplement of the present invention are preferably phytosterols, and preferably have a perhydrocyclopentanophenanthrene ring system as shown below in the compound of formula I:

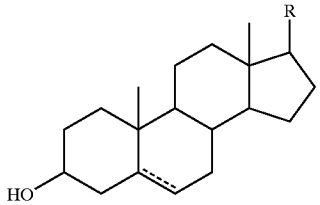

wherein the dashed line is a single or double bond and R is a $C_1$–$C_{10}$ alkyl, substituted ($C_1$–$C_{10}$)alkyl, ($C_2$–$C_{10}$)alkenyl or substituted ($C_2$–$C_{10}$)alkenyl group.

In the present application, the term "sterols" includes sterols in reduced form (stanols), preferably β-sitostanol or fucostanol (reduced fucosterol).

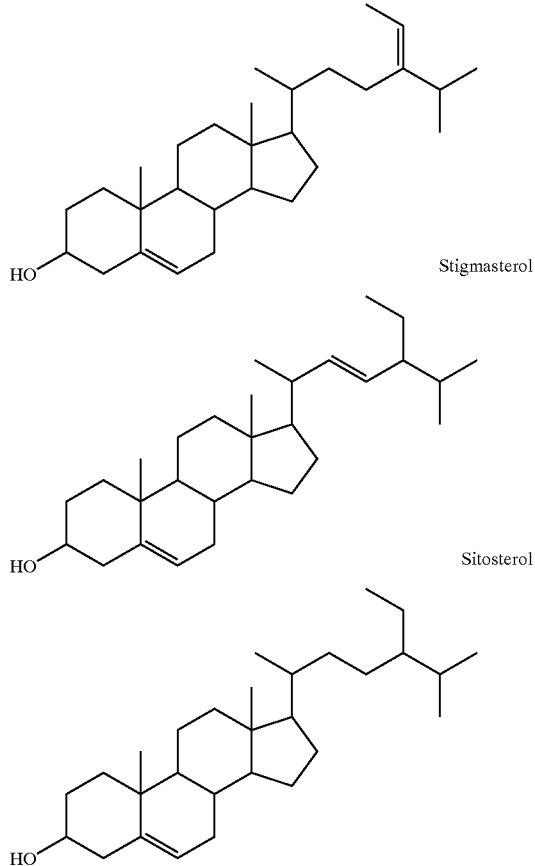

One or more sterols can be used to prepare the nutritional supplement. The term "phytosterols" includes sterols from terrestrial or marine plants, seaweed, microalgae, etc. Preferably, the sterol is stigmasterol, sitosterol, fucosterol, β-sitostanol or fucostanol.

Fucosterol is abundant in brown algae. Prior to esterification with the omega-3 fatty acid, fucosterol can be reduced to fucostanol. Preferably, the reduction is carried out using hydrogen gas in the presence of a suitable catalyst such as palladium on charcoal (Pd/C), but other reduction processes that ultimately yield a food-quality ester, after purification if necessary, may be used.

The nutritional supplement of the present invention comprises one or more omega-3 fatty acids, and is preferably an ester of an acid of the formula:

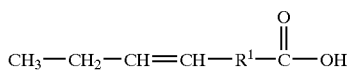

wherein $R^1$ is a ($C_3$–$C_{40}$)alkenylene group comprising at least one double bond, more preferably 2 to 5 double bonds. More preferably, the omega-3 fatty acid is stearidonic acid 18:4ω3 (SA), eicosapentaenoic acid 20:5ω3 (EPA) or docosahexaenoic acid 22:6ω3 (DHA).

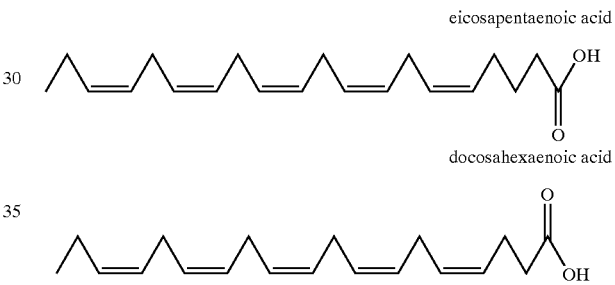

Omega-3 fatty acids, such as EPA and DHA, are long-chain polyunsaturated fatty acids (LCPUFAs) that are abundant in oily fish such as menhaden, salmon, tuna, and sardine, as well as in certain plants and microbes, such as particular fungi and microalgae. The preferred source of omega-3 fatty acids for the present invention is fish oil, more preferably a highly refined fish oil concentrate having approximately 65% omega-3 fatty acid content which is predominantly EPA and DHA in the form of triglyceride esters. These triglycerides are preferably converted to lower alkyl esters, such as methyl, ethyl or propyl esters, by known methods and used in an esterification with a sterol to form esters, which can be further purified necessary, for use as nutritional supplements.

The cardiovascular effects of dietary fish oils have long been recognized [18, 19]. Omega-3 fatty acids lower plasma triglyceride concentrations principally by inhibiting synthesis of triacylglycerol and VLDL by the liver [20]. In addition, omega-3 fatty acids are anti-thrombotic and are protective against cardiac arrhythmias [21]. The benefits of fish oil consumption are illustrated by the finding of the Diet and Reinfarction Trial (DART) which showed a reduction of 29% in the overall mortality in survivors of a first myocardial infarction who consumed fish rich in omega-3 fatty acids at least twice weekly [22]. Two recent studies demonstrate the efficacy of omega-3 fatty acid supplementation. In a randomized, double-blind, placebo-controlled trial patients with coronary artery disease who ingested a 1.5 g/day fish oil supplement (55% EPA and DHA) for two years had less progression and more regression of their disease based on coronary angiography compared to patients ingesting the placebo [23]. In the GISSI—Prevenzione trial, omega-3 fatty acid supplements in patients who had myocardial infarction reduced cardiovascular death by 30% [24]. Although omega-3 fatty acids are anti-atherogenic, they do not lower plasma cholesterol and in some incidences may slightly increase LDL-cholesterol [25]. Safety and toxicological studies spanning several years have shown that fish oils are safe to consume. Recently, fatty acids such as the omega-3 fatty acids from fish oil were granted GRAS (Generally Regarded As Safe) status in the United States, which permits their addition to foods low in long-chain polyunsaturated fatty acids. The typical North American diet contains about 0.15 grams omega-3 fatty acids whereas Inuit may ingest up to 10 grams of omega-3 fatty acids daily. A daily intake of 2 to 3 grams of omega-3 fatty acids has consistently been shown to lower plasma triglycerides [18]. Therefore, a suitable daily intake of omega-3 fatty acid in the present invention is about 0.1 to about 10 grams, preferably about 2 to about 3 grams, but clearly greater amounts can be tolerated, and may be beneficial.

Phytosterols are considered safe for human consumption. A typical daily intake in North America is about 100 to 300 milligrams. However, a dose of greater than 3 grams of the phytosterol esters are required to have significant impact on plasma cholesterol levels [13]. Such doses are safe with no known side effects. In the present invention, a preferred daily intake of phytosterol is about 2 to about 3 grams.

Phytosterol esters prepared using fish oil as the source of omega-3 fatty acids contain a significant amount of EPA and DHA. Such esters can simultaneously reduce serum cholesterol and serum triglyceride levels. The triglyceride-lowering ability of the omega-3 fatty acid component of the ester is dependent on its entry into the circulatory system. A lipid esterase in the intestinal lumen may be responsible for release of the omega-3 fatty acid from the phytosterol, which would make both species available for uptake into the circulatory system. There is a non-specific lipid esterase, secreted into the intestinal lumen during digestion that is active against a variety of molecular species including cholesterol esters, monoglycerides, and esters of vitamin A [26].

At least one edible additive, such as listed below, can be included for consumption with the nutritional supplement of the invention and may have, for example, antioxidant, dispersant, antimicrobial, or solubilizing properties. A suitable antioxidant is, for example, vitamin C, vitamin E or rosemary extract. A suitable dispersant is, for example, lecithin, an alkyl polyglycoside, polysorbate 80 or sodium lauryl sulfate. A suitable antimicrobial is, for example, sodium sulfite or sodium benzoate. A suitable solubilizing agent is, for example, a vegetable oil such as sunflower oil, coconut oil, and the like, or mono-, di- or tri-glycerides.

Additives include vitamins such as vitamin A (retinol, retinyl palmitate or retinol acetate), vitamin B1 (thiamin, thiamin hydrochloride or thiamin mononitrate), vitamin B2 (riboflavin), vitamin B3 (niacin, nicotinic acid or niacinamide), vitamin B5 (pantothenic acid, calcium pantothenate, d-panthenol or d-calcium pantothenate), vitamin B6 (pyridoxine, pyridoxal, pyridoxamine or pyridoxine hydrochloride), vitamin B12 (cobalamin or cyanocobalamin), folic acid, folate, folacin, vitamin H (biotin), vitamin C (ascorbic acid, sodium ascorbate, calcium ascorbate or ascorbyl palmitate), vitamin D (cholecalciferol, calciferol or ergocalciferol), vitamin E (d-alpha-tocopherol, or d-alpha tocopheryl acetate) and vitamin K (phylloquinone or phytonadione).

Other additives include minerals such as boron (sodium tetraborate decahydrate), calcium (calcium carbonate, calcium caseinate, calcium citrate, calcium gluconate, calcium lactate, calcium phosphate, dibasic calcium phosphate or tribasic calcium phosphate), chromium (GTF chromium from yeast, chromium acetate, chromium chloride, chromium trichloride and chromium picolinate) copper (copper gluconate or copper sulfate), fluorine (fluoride and calcium fluoride), iodine (potassium iodide), iron (ferrous fumarate, ferrous gluconate gluconate, magnesium hydroxide or magnesium oxide), manganese (manganese gluconate and manganese sulfate), molybdenum (sodium molybdate), phosphorus (dibasic calcium phosphate, sodium phosphate), potassium (potassium aspartate, potassium citrate, potassium chloride or potassium gluconate), selenium (sodium selenite or selenium from yeast), silicon (sodium metasilicate), sodium (sodium chloride), strontium, vanadium (vanadium surface) and zinc (zinc acetate, zinc citrate, zinc gluconate or zinc sulfate).

Other additives include amino acids, peptides, and related molecules such as alanine, arginine, asparagine, aspartic acid, carnitine, citrulline, cysteine, cystine, dimethylglycine, gamma-aminobutyric acid, glutamic acid, glutamine, glutathione, glycine, histidine, isoleucine, leucine, lysine, methionine, ornithine, phenylalanine, proline, serine, taurine, threonine, tryptophan, tyrosine and valine.

Other additives include animal extracts such as cod liver oil, marine lipids, shark cartilage, oyster shell, bee pollen and d-glucosamine sulfate.

Other additives include unsaturated free fatty acids such as γ-linoleic, arachidonic and α-linolenic acid, which may be in an ester (e.g. ethyl ester or triglyceride) form.

Other additives include herbs and plant extracts such as kelp, pectin, Spirulina, fiber, lecithin, wheat germ oil, safflower seed oil, flax seed, evening primrose, borage oil, blackcurrant, pumpkin seed oil, grape extract, grape seed extract, bark extract, pine bark extract, French maritime pine bark extract, muira puama extract, fennel seed extract, dong quai extract, chaste tree berry extract, alfalfa, saw palmetto berry extract, green tea extracts, angelica, catnip, cayenne, comfrey, garlic, ginger, ginseng, goldenseal, juniper berries, licorice, olive oil, parsley, peppermint, rosemary extract, valerian, white willow, yellow dock and yerba mate.

Other additives include enzymes such as amylase, protease, lipase and papain as well as miscellaneous substances such as menaquinone, choline (choline bitartrate), inositol, carotenoids (beta-carotene, alpha-carotene, zeaxanthin, cryptoxanthin or lutein), para-aminobenzoic acid, betaine HCl, free omega-3 fatty acids and their esters, thiotic acid (alpha-lipoic acid), 1,2-dithiolane-3-pentanoic acid, 1,2-dithiolane-3-valeric acid, alkyl polyglycosides, polysorbate 80, sodium lauryl sulfate, flavanoids, flavanones, flavones, flavonols, isoflavones, proanthocyanidins, oligomeric proanthocyanidins, vitamin A aldehyde, a mixture of the components of vitamin $A_2$, the D Vitamins ($D_1$, $D_2$, $D_3$ and $D_4$) which can be treated as a mixture, ascorbyl palmitate and vitamin $K_2$.

The nutritional supplement of the invention is typically a viscous oil and can be added to a foodstuff composition during processing of the foodstuff. Such a foodstuff composition is often referred to as a functional food, and can be any food that will tolerate the physicochemical properties of the nutritional supplement, for example, margarine, cooking oil, shortening or mayonnaise. It can also be packaged for consumption in softgel, capsule, tablet or liquid form. It can be supplied in edible polysaccharide gums, for example carrageenan, locust bean gum, guar, tragacanth, cellulose and carboxymethylcellulose.

The nutritional supplement can also be microencapsulated. Microencapsulation can be carried out, for example, using a gelatin such as bovine gelatin in a co-extrusion process, prior to processing into a foodstuff composition, for example baked goods, candy, margarines and spreads, ice cream, yogurts, frozen desserts, cake mixes and pudding mixes. The packaging of the nutritional supplement should preferably provide physical protection from such effects as pH, particularly basic conditions, oxidation and degradation by light. This latter effect can be minimized for example by changing the mesh size of the microencapsulation or inclusion of a suitable dye. The nutritional supplement can also be stored in a light-opaque container to minimize photodegradation.

The example below describes synthesis of an ester of the invention. The ester linkage can be formed according to known methods, such as by esterification of free fatty acids by sterols or stanols under acid catalysis (U.S. Pat. No. 5,892,068: Higgins III, issued Apr. 6, 1999). Preferably, however, a base is used as a catalyst to promote transesterification. More preferably, the base is a metal ($C_1$–$C_{10}$) alkoxide, even more preferably sodium methoxide or ethoxide. Conveniently, the reactants are heated to a temperature of about 100° C. to about 200° C. with stirring, preferably under reduced pressure, for about 30 minutes to about 4 hours. The base is then added and the mixture conveniently stirred at a temperature of about 100° C. to about 200° C. under reduced pressure for about 30 minutes to about 36 hours. Alternatively, the starting ester is heated to a temperature of about 100° C. to about 200° C. with stirring, preferably under reduced pressure, for about 30 minutes to about 4 hours. The base dispersed in the phytosterol is then added and the mixture conveniently stirred at a temperature of about 100° C. to about 200° C. under reduced pressure for about 30 minutes to about 36 hours. The ester that is formed can be further purified if necessary for use as a nutritional supplement.

The further purification is preferably carried out by precipitation and extraction, preferably sequentially, using two immiscible solvents. Unreacted sterol is precipitated by addition of a suitable non-polar solvent and filtered off. A suitable non-polar solvent can be an aliphatic liquid such as a liquid alkane, preferably pentane, hexane, heptane, octane, isooctane or dodesane, more preferably hexane. Corresponding fluoroalkanes can also be used. The non-polar solvent can also be an aromatic solvent such as benzene or toluene, or an other solvent of similar polarity such as carbon tetrachloride or methyl-tert-butyl ether.

The filtrate is then extracted by a suitable extraction solvent to remove unreacted omega-3 fatty acid-containing material. The extraction solvent is preferably a polar solvent such as methanol, ethanol or ethylene glycol dimethyl ether (monoglyme), more preferably methanol. Certain dipolar aprotic solvents, such as N,N-dimethyl formamide (DMF) or dimethylsulfoxide (DMSO), can also be used.

EXAMPLE 1

Synthesis of Stigmasterol/Omega-3 Fatty Acid Esters (A) A mixture of dry stigmasterol (3 g, 7.27 mmol) and a highly concentrated mixture of EPA and DHA omega-3 fatty acids in ethyl ester form (EPAX™ 5500, ProNova; 4.3 g, 12.6 mmol) were heated while being stirred magnetically at 140 to 145° C. for 2 hours under vacuum (5 mm). Subsequently the vacuum was disconnected and powdered sodium methoxide (40 mg, 0.75 mmol) was added quickly in one portion. The vacuum was connected immediately and the mixture was stirred at 140 to 145° C. for an additional 4 hours. Hexane (25 mL) was added to precipitate the residual stigmasterol and the mixture was centrifuged for 5 minutes at 15,000 g (0° C.), the supernatant was removed and the pellet was washed again with 5 mL of hexane. The remaining precipitate was centrifuged off and the supernatants combined. The organic phase was washed with water (5 mL), dried over sodium sulfate and the solvent removed under reduced pressure. TLC (hexane/diethylether/acetic acid (90:10:1), $R_f$ 0.71. The yield was 5.9 g (85%). The ester product was a viscous oil.

When the experiment was repeated using freshly made sodium ethoxide, almost the same level of conversion was obtained as with sodium methoxide. However, this was not seen with commercially available sodium ethoxide, which performed more poorly than sodium methoxide.

Synthesis of Stigmasterol/Omega-3 Fatty Acid Esters (B) A highly concentrated mixture of EPA and DHA omega-3 fatty acids in ethyl ester form (EPAX™5500 EE, BioNova; 221 g, 649 mmol) was heated while being stirred magnetically at 140 to 145° C. for 2 hours under vacuum (5 mm). A well dispersed mixture of dry stigmasterol (268 g, 649 mmol) and sodium methoxide (40 mg, 0.75 mmol) was added portionwise within 1 hour and the mixture was stirred at 170 to 175° C. for an additional 21 hours. The reaction mixture was liberated from unreacted material either by column chromatography (2% diethylether in hexane on silicagel) or by a sequential extraction using two immissible solvents. The unreacted stigmasterol was precipitated upon addition of hexane and the solution was then filtered. The filtrate was extracted with methanol to remove unreacted starting oil material. TLC (hexane/diethylether/acetic acid (90:10:1) gave an $R_f$ equal to 0.71. The yield was 434 g (70%). The ester product was a viscous oil.

When the experiment was repeated using freshly made sodium ethoxide, almost the same level of conversion was obtained as with sodium methoxide. However, this was not seen with commercially available sodium ethoxide, which performed more poorly than sodium methoxide.

The procedure works also from a concentrated mixture of EPA and DHA omega-3 fatty acids in triglyceride form (EPAX™5500 TG, BioNova) with a similar yield of final product.

EXAMPLE 2

The Effect of a Phytosterol-Fish Oil Ester-Containing Diet on Plasma Lipid Levels in Guinea Pigs Guinea pigs were chosen for this project, as their blood lipid profiles and responses to dietary manipulation more closely resemble those of humans than do more commonly used laboratory rodents. Two groups of eight guinea pigs each were fed a standard, non-purified guinea pig chow (Prolab guinea pig 5 P18, PMI Nutrition International, Inc., Brentwood, Mo.). Baseline values for blood lipids were determined and then the animals were placed on a control diet (Group 1) or a phytosterol-fish oil ester-containing diet (Group 2).

Phytosterol-fish oil esters were prepared as described in Example 1 and mixed 5:1 with corn oil. This was incorporated into crushed chow to give a concentration of phytosterol-fish oil esters of 2.5% (w/w). Control diet was prepared using an equivalent amount of corn oil. Both control and test diets were supplemented with 0.08% cholesterol. The chow was re-pelleted using a Hobart extruder. Food was stored in sealed plastic bags with nitrogen purging at −20° C. in the dark. Fresh food was prepared each week.

Blood samples were collected from each animal after 2 and 4 weeks for determination of plasma lipids (total cholesterol, HDL-cholesterol, non-HDL-cholesterol, and triacylglycerols).

Guinea pigs fed phytosterol-fish oil esters (2.5% g/100 gram diet) had significantly lower levels of plasma total cholesterol and triacylglycerol compared to control fed animals after 4 weeks of feeding (Table 1). At this time, plasma cholesterol and triacylglycerols were 36% and 29% lower in the treatment group. A statistically significant effect of phytosterol-fish oil esters on cholesterol was also evident after 2 weeks where the reduction was 30% compared to the control value. The changes in cholesterol level could be completely explained by changes in the amount of non-high density lipoprotein (HDL)-cholesterol (Table 2). Non-HDL cholesterol was 30% and 38% lower in the phytosterol-fish oil ester-fed group at 2 and 4 weeks, respectively, whereas there were no differences in HDL-cholesterol.

These results illustrate the ability of dietary phytosterol-fish oil esters to reduce the levels of plasma cholesterol and triacylglycerol. It is also shown that phytosterol-fish oil esters lower non-HDL cholesterol ("bad cholesterol") but do not affect the level of HDL ("good cholesterol").

TABLE 1

The effect of a phytosterol/fish oil esters containing diet on plasma total cholesterol and triacylglycerol levels in guinea pigs

|  |  | Total Cholesterol | Triacylglycerol |
|---|---|---|---|
| Group 1 | Week 2 | 1.72 ± 0.38 | 0.92 ± 0.26 |
|  | Week 4 | 2.05 ± 0.20 | 0.87 ± 0.16 |
| Group 2 | Week 2 | 1.22 ± 0.10* | 0.77 ± 0.22 |
|  | Week 4 | 1.32 ± 0.20* | 0.62 ± 0.13* |

Results are mean ± S.D. of 8 guinea pigs per group. The baseline values for plasma total cholesterol and triacylglycerol were 1.28 ± 0.12 (mM) and 0.65 ± 0.11 (mM) respectively.
*Significantly lower than the corresponding value for Group 1 ($p < 0.05$; Bonferroni's Multiple Comparison Test).

TABLE 2

The effect of a phytosterol/fish oil esters containing diet on lipoprotein metabolism in guinea pigs

|  |  | HDL Cholesterol | non-HDL Cholesterol |
|---|---|---|---|
| Group 1 | Week 2 | 0.14 ± 0.03 | 1.58 ± 0.4 |
|  | Week 4 | 0.16 ± 0.06 | 1.90 ± 0.2 |
| Group 2 | Week 2 | 0.11 ± 0.04 | 1.11 ± 0.14* |
|  | Week 4 | 0.16 ± 0.03 | 1.17 ± 0.23* |

Results are mean ± S.D. of 8 guinea pigs per group. The baseline values for HDL cholesterol and non-HDL cholesterol were 0.16 ± 0.07 (mM) and 1.14 ± 0.16 (mM) respectively.
*Significantly lower than the corresponding value for Group 1 ($p < 0.05$; Bonferroni's Multiple Comparison Test).

EXAMPLE 3

The Effect of a Phytosterol-Fish Oil Ester-Containing Diet on Plasma Lipid Levels in an Obese Rat Model The efficacy of a phytosterol-fish oil ester-containing diet to lower plasma triacylglycerol and cholesterol was studied in the JCR:La-cp (corpulent) rat, a genetic model of obesity (O'Brien and Russell, 1997). Animals of this strain, if homozygous for the autosomal recessive cp gene (cp/cp), are obese, insulin resistant, hyperinsulinemic, and highly hypertriglyceridemic. In addition the obese animals exhibit poor vascular responsiveness and develop ischemic lesions of the myocardium with age. Rats that are homozygous normal or heterozygous (−/?), are lean and metabolically normal. The effect of phytosterol-fish oil ester feeding was determined using obese (cp/cp) rats at 8 weeks of age, when the rats are clearly obese and fully insulin resistant. Lean littermates (+/?) of the obese animals were included in the study as benchmark for comparison. Obese animals were fed one of four diets: a control diet containing no added oil (Group 1); a control diet containing 2.6 g/kg canola (Group 2); or diets containing 0.5 or 2.6 g/kg phytosterol-fish oil ester (Group 3 and Group 4, respectively). The lean animals (Group 5) received the control without canola. The various test diets were fed for four weeks.

Preparation of the diets using standard rat chow (Rodent Diet 5001, PMI Nutrition International, St Louis, Mo.) was essentially the same as described in Example 2. Phytosterol-fish oil ester was mixed with canola oil (5:1) and the oil mixture was added to the powered diet at a concentration of 0.5 g/kg or 2.6 g phytosterol ester/kg diet, which was then pelleted. Control diets contained no added oil or 2.6 g/kg canola oil. Food was stored in sealed plastic bags with nitrogen purging and maintained at 4° C. Fresh food was prepared each week.

Blood samples were collected from each animal at the start and after 4 weeks for determination of plasma lipids (total cholesterol, cholesterol esters, phospholipids, and triacylglycerols).

Obese JCR-La rats exhibit marked hypertriglyceridemia and elevated plasma cholesterol levels compared to their lean littermates (Group 1 or 2 versus Group 5; Table 3). There was a concentration-dependent effect of dietary phytosterol-fish oil esters on plasma lipid concentrations. The lower dose of 0.5 g phytosterol-fish oil ester/kg food had no impact on lipid parameters in animals fed for 4 weeks (Group 3 versus Group 2 at 12 weeks; Table 3). However 2.6 g phytosterol-fish oil ester/kg food reduced triacylglyerol level from control levels by 51% (1.26 mM versus 2.59 mM in the control). Although this is a marked reduction, the animals are still strongly hypertriglycemic (Group 4 versus Group 5). There was also a modest reduction of cholesterol levels in animals fed the high dose of phytosterol-fish oil ester (13% reduction in total cholesterol; 17% reduction in cholesterol esters). There was a tendency for phospholipid values to be reduced in phytosterol-fish oil ester-fed animals but this did not reach statistical significance.

The results show that phytosterol-fish oil esters decrease plasma triacylglyerol and cholesterol in obese JCR-La rats and that this occurs in a dose-dependent manner. The reduction in triacylglycerol and cholesterol esters is consistent with a substantial reduction in very low density lipoprotein (VLDL) particles through a decreased rate of VLDL production by the liver. These improvements in lipid profile might also be expected to have a beneficial effect on the insulin-resistant state of these animals.

TABLE 3

Whole serum lipid concentrations in high dose ON-1-treated male JCR-LA-cp rate

| | Free Cholesterol | Cholesteryl esters | Total cholesterol | Phospholipids | Triacylglycerols |
|---|---|---|---|---|---|
| Initial values at 8 weeks of age: | | | | | |
| Group 1 (no oil control) | 0.73 ± 0.11 | 1.19 ± 0.39 | 2.63 ± 0.49 | 2.19 ± 0.36 | 2.06 ± 1.19 |
| Group 2 (oil control) | 0.68 ± 0.10 | 1.89 ± 0.31 | 2.58 ± 0.40 | 2.01 ± 0.20 | 1.37 ± 0.63 |
| Group 3 (0.5 mg/kg dose) | 0.75 ± 0.12 | 2.01 ± 0.19 | 2.76 ± 0.30 | 2.35 ± 0.33 | 2.17 ± 1.11 |
| Group 4 (2.6 mg/kg dose) | 0.74 ± 0.09 | 1.94 ± 0.24 | 2.67 ± 0.33 | 2.28 ± 0.27 | 2.64 ± 0.84 |
| Group 5 (lean control) | 0.48 ± 0.06 | 1.31 ± 0.09 | 1.79 ± 0.12 | 1.01 ± 0.13 | 0.25 ± 0.16 |
| Final values at 12 weeks of age: | | | | | |
| Group 1 (no oil control) | 0.67 ± 0.06 | 1.58 ± 0.24 | 2.25 ± 0.29 | 1.92 ± 0.27 | 2.58 ± 0.93 |
| Group 2 (oil control) | 0.60 ± 0.09 | 1.61 ± 0.16 | 2.21 ± 0.23 | 1.87 ± 0.22 | 2.59 ± 0.58 |
| Group 3 (0.5 mg/kg dose) | 0.62 ± 0.14 | 1.55 ± 0.26 | 2.17 ± 0.37 | 1.90 ± 0.26 | 2.51 ± 0.71 |
| Group 4 (2.6 mg/kg dose) | 0.58 ± 0.06 | 1.34 ± 0.11** | 1.92 ± 0.15* | 1.66 ± 0.19 | 1.26 ± 0.72** |
| Group 5 (lean control) | 0.34 ± 0.03 | 0.90 ± 0.04 | 1.24 ± 0.06 | 0.71 ± 0.04 | 0.17 ± 0.04 |

Values are mmol/l; mean ± S.D., 8 rats in each group.
**Significantly lower compared to group 2 ($P < 0.05$).

REFERENCES

1 Criqui, M. H. Triglycerides and cardiovascular disease: a focus on clinical trials. (1998) Eur Heart Journal 19 (Suppl A), A36–A39.

2 Grundy, S. M. Small LDL, atherogenic dyslipidemia, and the metabolic syndrome. (1997) Circulation 95, 1–4.

3 Grundy, S. M. Hypertriglyceridemia, atherogenic dyslipidemia, and the Metabolic Syndrome. (1998) Am J Cardiol 81, 18B–25B.

4 Gotto Jr., A. M. Triglyceride: the forgotten risk factor. (1998) Circulation 97, 1027–1028.

5 Jeppeson, J., Hein, O. H., Suadicani, P. and Gyntelberg, F. Triglyceride concentration and ischemic heart disease: an eight-year follow-up in the Copenhagen male study. (1998) Circulation 97, 1029–1036.

6 Franceschini, G. and Paoletti, R. Pharmacological control of hypertriglyceridemia. (1993) Cardiovasc Drugs Ther 7, 297–302.

7 Eisenberg, D. The importance of lowering cholesterol in patients with coronary heart disease. (1998) Clin Cardiol 21, 81–84.

8 Scandinavian Simvastatin Survival Study Group. Randomised trial of cholesterol lowering in 4444 patients with coronary heart disease: the Scandinavian Simvastatin Survival Study (4S). (1994) Lancet 344, 1383–1389.

9 Shepherd, J., Cobbe, S. M., Ford, I., Isles, C. G., Lorimer, A. R., MacFarlane, P. W., McKillop, J. H. and Packard, C. J. Prevention of coronary heart disease with pravastatin in men with hypercholesterolemia. (1995) N Engl J Med 333, 1301–1307.

10 Sacks, F. M., Pfeffer, M. A., Moye, L. A., Rouleau, J. L., Rutherford, J. D., Cole, T. G., Brown, L., Warnica, J. W., Arnold, J. M. O., Wun, C., Davis, B. R. and Braunwald, E. The effect of pravastatin on coronary events after myocardial infarction in patients with average cholesterol levels. (1996) N Engl J Med 335, 1001–1009.

11 Heinemann, T., Kullak-Ublick, G. A., Pietruck, B. and von Bergmann, K. Mechanisms of action of plant sterols on inhibition of cholesterol absorption: comparison of sitosterol and sitostanol. (1991) Eur J Clin Pharmacol 40 (Suppl 1), S59–S63.

12 Ling, W. H. and Jones, P. J. H. Dietary phytosterols: a review of metabolism, benefits and side effects. (1995) Life Sci 57, 195–206.

13 Jones, P. J. H., MacDougall, D. E., Ntanios, F. and Vanstone, C. A. Dietary phytosterols as cholesterol-lowering agents in humans. (1997) Can J Physiol Pharmacol 75, 217–227.

14 Vanhanen, H. T., Blomqvist, S., Ehnholm, C., Hyvonen, M., Jauhiainen, M., Torstila, I. and Miettnen, T. A. Serum cholesterol, cholesterol precursors, and plant sterols in hypercholesterolemic subjects with different apoE phenotypes during dietary sitostanol ester treatment. (1993) J Lipid Res, 1535–1544.

15 Heinemann, T., Leiss, O. and von Bergmann, K. Effect of low-dose sitostanol on serum cholesterol in patents with hypercholesterolemia. (1986) Atherosclerosis 61, 219–223.

16 Miettinen, T. A. and Gylling, H. Regulation of cholesterol metabolism by dietary plant sterols. (1999) Curr Opin Lipidol 10, 9–14.

17 Vanhanen, H. T., Kajander, J., Lehtovirta, H. and Miettinen, T. A. Serum levels, absorption efficiency, faecal elimination and synthesis of cholesterol during increasing doses of dietary sitostanol esters in hypercholesterolaemic subjects. (1994) Clin Sci 1994 87, 61–67.

18 Leaf, A. and Weber, P. C. Cardiovascular effects of n-3 fatty acids. (1988) N Engl J Med 318, 549–557.

19 Mishkel, G. J. and Cairns, J. A. Cardiovascular effects of w-3 polyunsaturated fatty acids (fish oils). (1990) Bailliere's Clin Haematol 3, 625–649.

20 Kinsella, J. E., Lokesh, B. and Stone, R. A. Dietary n-3 polyunsaturated fatty acids and amelioration of cardiovascular disease: possible mechanisms. (1990) Am J Clin Nutr 52, 1–28.

21 Connor, S. L. and Connor, W. E. Are fish oils beneficial in the prevention and treatment of coronary artery disease? (1997) Am J Clin Nutr 66 (Suppl), 1020S–1031S.

22 Burr, M. L., Fehily, A. M., Gilbert, J. F., Rogers, S., Holliday, R. M., Sweetnam, P. M., Elwood, P. C. and Deadman, N. M. Effects of changes in fat, fish, and fibre intakes on death and myocardial reinfarction: diet and reinfarction trial. (1989) Lancet 30, 757–761.

23 von Schacky, C., Angerer, P., Kothny, W., Theisen, K. and Mudra, H. The effect of dietary omega-3 fatty fcids on coronary atherosclerosis: A randomized, double-blind, placebo-controlled trial. (1999) Ann Intern Med 130, 554–562.

24 GISSI-Prevenzione Investigators. Dietary supplementation with n-3 polyunsaturated fatty acids and vitamin E after myocardial infarction: results of the GISSI-Prevenzione trial. (1999) Lancet 354, 447–455.

25 Harris, W. S. Fish oils and plasma lipid and lipoprotein metabolism in humans: a critical review. (1989) J Lipid Res 30, 785–807.

26 Carey, M. C., Small, D. M. and Bliss, C. M. Lipid digestion and absorption. (1983) Annu Rev Physiol 45, 651–677.

What is claimed is:

1. A process for preparing an ester comprising the step of reacting a sterol with an omega-3 fatty acid, wherein the omega-3 fatty acid comprises eicosapentaenoic acid 20:5ω3 (EPA), docosahexaenoic acid 22:6ω3 (DHA), an ester thereof, or a mixture thereof, and the sterol is stigmasterol, in the presence of a base.

2. The process of claim 1, wherein the omega-3 fatty acid is eicosapentaenoic acid 20:5ω3 (EPA).

3. The process of claim 1, wherein the omega-3 fatty acid is docosahexaenoic acid 22:6ω3 (DHA).

4. The process of claim 1, wherein the omega-3 fatty acid comprises a mixture of eicosapentaenoic acid 20:5ω3 (EPA) and docosahexaenoic acid 22:6ω3 (DHA).

5. The process of claim 1, wherein the ester of the omega-3 fatty acid is a triglyceride ester.

6. The process of claim 1, wherein the ester of the omega-3 fatty acid is an ethyl ester.

7. The process of claim 1, wherein the base is a metal ($C_1$–$C_{10}$) alkoxide.

8. The process of claim 7, wherein the metal ($C_1$–$C_{10}$) is sodium methoxide.

9. The process of claim 1, further comprising the step of precipitating unreacted sterol with a suitable non-polar solvent, and filtering off the precipitated unreacted sterol to leave a filtrate.

10. The process of claim 9, wherein the non-polar solvent is hexane.

11. The process of claim 9, further comprising the step of extracting the filtrate with a suitable immiscible solvent to remove unreacted omega-3 fatty acid, or an ester thereof, from the filtrate.

12. The process of claim 11, wherein the immiscible solvent is methanol.

* * * * *